United States Patent [19]

Dusel et al.

[11] Patent Number: 4,649,621

[45] Date of Patent: Mar. 17, 1987

[54] WIRE PROCESSING APPARATUS HAVING CONTROL MEANS

[75] Inventors: Robert O. Dusel, Brookfield; Harold J. Keene, Milwaukee, both of Wis.

[73] Assignee: Artos Engineering Company, New Berlin, Wis.

[21] Appl. No.: 831,533

[22] Filed: Feb. 21, 1986

[51] Int. Cl.[4] ............................................. H01R 43/04
[52] U.S. Cl. ................................... 29/564.4; 29/707; 29/720; 81/9.51; 356/394; 382/8
[58] Field of Search ...................... 29/564.4, 748, 747, 29/707, 720; 81/9.51; 356/394, 237; 358/101; 382/8, 14; 250/562, 563

[56] References Cited

U.S. PATENT DOCUMENTS

| | | | |
|---|---|---|---|
| 3,795,962 | 3/1974 | Baldyga | 29/707 |
| 4,072,928 | 2/1978 | Wilder | 382/8 |
| 4,087,908 | 5/1978 | Fuslo et al. | 29/564.4 |
| 4,343,553 | 8/1982 | Nakagawa | 356/376 |
| 4,399,554 | 8/1983 | Perkins et al. | 382/8 |
| 4,414,566 | 11/1983 | Peyton et al. | 358/101 |
| 4,479,145 | 10/1984 | Azuma | 358/101 X |
| 4,499,649 | 2/1985 | Maxner | 29/566.3 |
| 4,555,799 | 11/1985 | Kodama | 350/563 X |

FOREIGN PATENT DOCUMENTS

| | | | |
|---|---|---|---|
| 60249 | 4/1982 | Japan | 250/563 |
| 135440 | 8/1983 | Japan | 250/562 |

Primary Examiner—William R. Briggs
Attorney, Agent, or Firm—James E. Nilles; Nicholas A. Kees

[57] ABSTRACT

Wire processing apparatus employs a conveyor for transporting wire segments to a series of wire processing machines which strip insulation from the wire segment ends and then subsequently attach electric terminals to the stripped ends. A quality control device located between the insulation stripper machine and the terminal attachment machine inspects each stripped end and, if it does not meet desired tolerances, sends signals which prevent the terminal attachment machine from operating upon the defective stripped end as the conveyor moves the wire segment therepast. The quality control device comprises an illuminated field at which the stripped end momentarily stops, an optical lens opposite the illuminated field for providing an optical image of the stripped end, and a converter for converting the optical image to an electronic image signal. Solid state electronic circuits compare the image signal to a reference signal, provide an error signal if the stripped end is defective and store the error signal in a memory circuit. The error signal, if present, is recalled from the memory at the appropriate time and converted to an output signal which prevents the downstream terminal attachment machine from operating on the defective wire end.

16 Claims, 3 Drawing Figures

WIRE PROCESSING APPARATUS HAVING CONTROL MEANS

BACKGROUND OF THE INVENTION

This invention relates generally to wire processing apparatus having control means, such as apparatus in which wire segments are conveyed to wire processing machines which strip insulation from the segment ends and attach terminals thereto. In particular, it relates to wire processing apparatus with control means having an optical device and associated circuitry for determining whether or not a stripped end meets desired parameters and for preventing operation of the terminal attachment machine if it does not.

Optical systems for inspecting manufactured products are well known. For instance, Perkins III et al., U.S. Pat. No. 4,399,554, describes an apparatus for inspecting the valve retainer assemblies of an engine head to ensure that each such assembly has its full complement of valve spring retainer keys. Another example is Wilder, U.S. Pat. No. 4,072,928, which discloses a system for inspecting workpieces and identifying them based on markings on the workpieces optically detected and distinguished by means of associated logic circuits. This latter system is even trainable, by relatively unskilled workers, by exposing the system to sample markings of the same general type as the markings on the workpieces to be ultimately inspected.

There is need in the market, however, for a wire processing apparatus having quality control means, which is inexpensive and simple to operate, for inspecting wire segment stripped ends to determine which are properly stripped and should continue to be processed, and which are not properly stripped and should not be further processed.

SUMMARY OF THE INVENTION

The wire processing apparatus of the present invention includes a stepwise conveyor for moving wire segments from one to the next of a series of stations of wire processing machines, stopping at each station for processiong. One of the wire processing machines strips insulation from the wire segment ends. A subsequent machine attaches electric terminals to the stripped ends. A quality control means is located at a step between the two other machines to inspect each stripped end and determine whether or not it meets certain desired tolerances. If it does not, the terminal attachment machine is prevented from operating on the particular defective stripped end when that end reaches that machine. The quality control means includes an optical lens positioned opposite an illuminated field. The stripped wire end to be inspected is conveyed between the illuminated field and the lens and momentarily stopped in that position. The lens produces an optical image, and associated circuitry converts that image to an electronic image signal. Main processor circuitry compares the image signal to a reference signal, provides an error signal if the image signal and reference signal do not match within certain predetermined tolerances, and stores any such error signal in a memory circuit. At the appropriate time, that is, when the particular wire end reaches the terminal attachment machine, the memory circuit is tested. If the error signal is present with respect to the particular wire end under consideration, the terminal attachment machine is prevented from operating on the defective wire end. The quality control means also includes a monitor screen to which the electronic image signal is passed, whether or not an error signal is generated. Thus a human operator can view a display of each wire end to check on the operation of the wire processing apparatus at his discretion. The reference signal which defines defect parameters is entered by means of a "learn mode". In the learn mode, a properly stripped wire end is viewed by the quality control device, and the human operator issues a learn command. This causes the quality control device to store the electronic image signal of the properly stripped wire end as the reference signal for comparison to all subsequent wire ends. The comparison is done according to tolerances entered by the operator using a keyboard, thumbwheel switches or other input devices. The control means also has the capability of stopping the conveyor if a predetermined number of defective stripped ends appear or if no ends at all appear on the conveyor for a predetermined number of conveyor steps.

DESCRIPTION OF THE PREFERRED EMBODIMENTS

Figure 1:
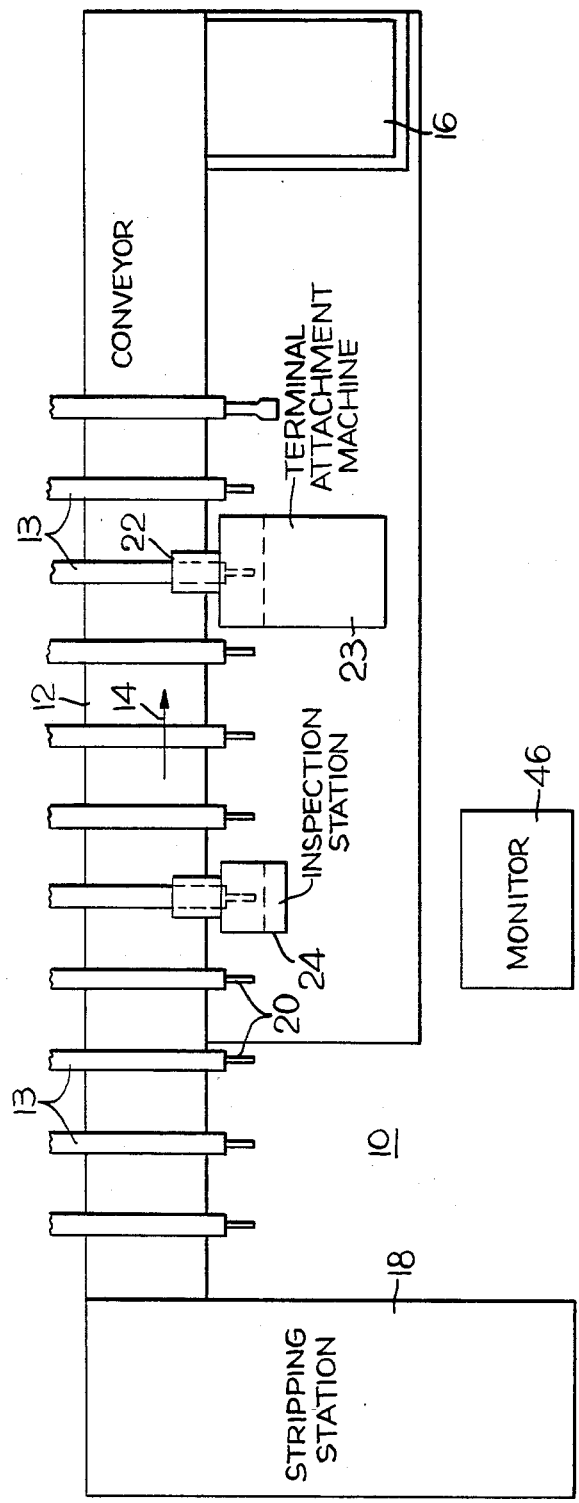
FIG. 1 is a top view of the wire processing apparatus according to one embodiment of the invention.

Referring now to FIG. 1, the wire processing apparatus 10 of the present invention includes various wire processing stations distributed along a stepwise conveyor 12, that is, a conveyor which transports wire segments 13 along a path in steps in the direction indicated by arrow 14, by means of a drive unit 16, stopping at regular intervals so that certain tasks may be accomplished on the wire segments 13. Although the conveyor 12 shown is a linear conveyor, it is not necessary that the conveyor be linear. The path along which the wire segments are conveyed could be curved or shaped in any suitable manner. In particular, the first station is a wire stripping machine 18 for stripping insulation from an end 20 of wire segment 13, when conveyor 12 is stopped with end 20 at station 18, to provide a stripped wire end 20 having certain predetermined characteristics as to size and quality. A second station 22, located downstream from the wire stripping station 18, is a machine for further processing the wire end 20 after it has been stripped and while the conveyor 12 is stopped with the wire end 20 located at the station 22. Any suitable wire processing machine may be located at station 22, such as a tinning station or, as shown at FIG. 1, a terminal attachment machine 23. The terminal attachment machine 23 starts the terminal attachment operation when an end 20 reaches station 22. Located along the conveyor 12, between the stripping station 18 and the second station 22, is an inspection station 24 for inspecting wire segment stripped ends 20 as they leave the stripping station 18, to ensure that the ends are properly stripped before terminals are attached thereto at station 22.

Figure 2:
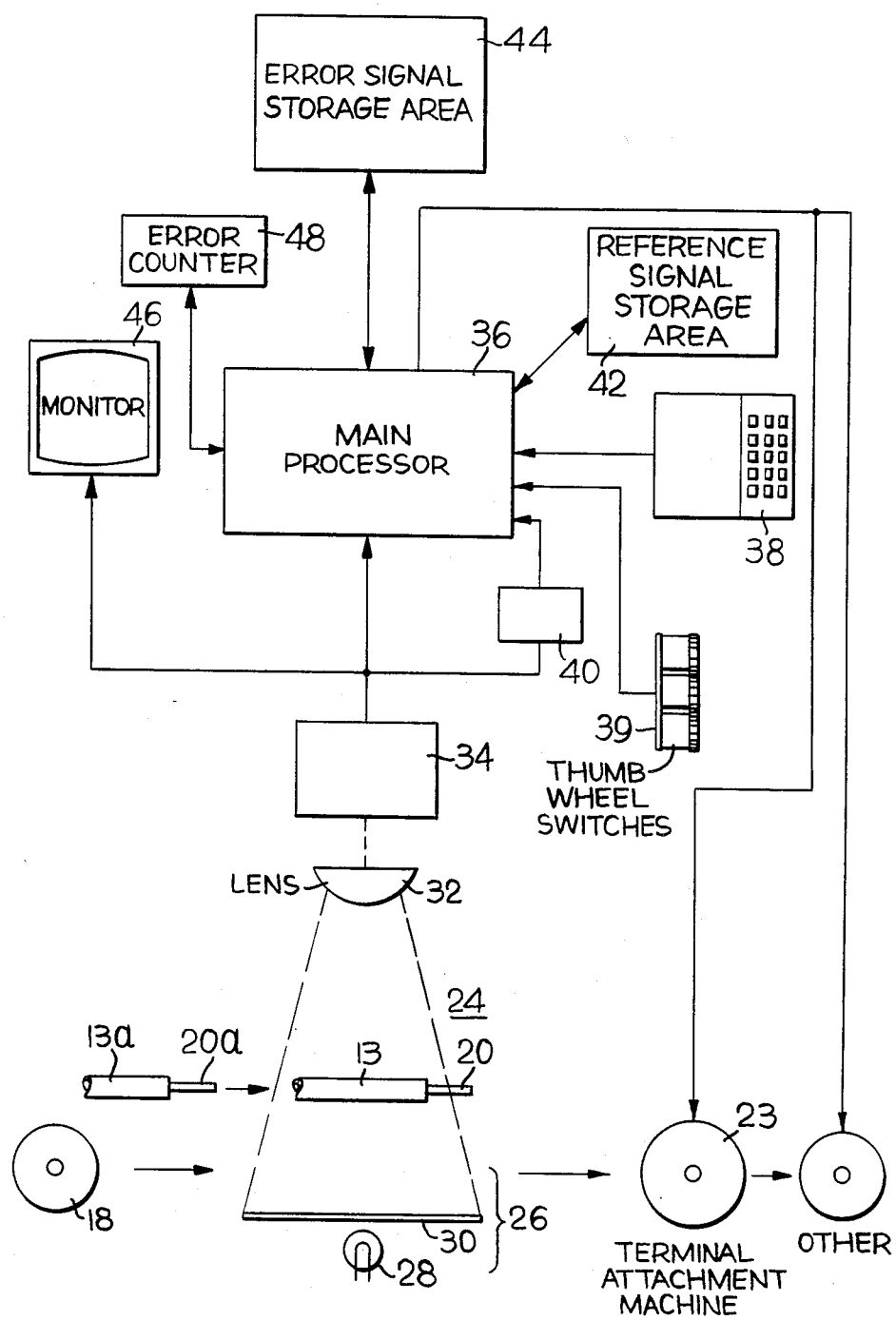
FIG. 2 is a schematic diagram of a control which employs the present invention for control of wire processing apparatus.

FIG. 2 is a schematic diagram of the apparatus 10, showing detail of the inspection station 24. As can be seen in that figure, inspection station 24 includes an illuminated field 26 past which each stripped wire end 20 is conveyed. The illuminated field 26 preferably includes a light source 28, with a preferably translucent surface 30 located between the light source 28 and the stripped wire end 20. An optical lens 32 is located opposite the illuminated field 26 so that the stripped wire ends 20 are conveyed between field 26 and lens 32. The lens 32 is attached to a converter 34, which converts the optical image of the stripped wire end 20 to an electronic image signal which represents the optical image. The converter 34 may employ any suitable means to accomplish the conversion. The converter 34 then sends the image signal to a main processor unit 36. The main processor unit 36 has previously received information as to parameters of a properly stripped wire end from a human operator (not shown) via a "learn mode". This "learn mode" is entered by the processor 36 when the operator issues a "learn" command, such as by pressing a "learn" button on the keyboard 38 or other input device 40. The main processor 36 then stores the image signal as the reference signal in a reference signal memory area 42, and the reference signal is recalled for comparison to the image signal representing any subsequent stripped wire end 20 by main processor 36. Thereafter, whenever another stripped wire end 20a is conveyed into position between the lens 32 and the illuminated field 26, the image signal corresponding thereto is compared to the reference signal stored in the reference signal memory area 42 to determine whether or not the particular stripped wire end 20a matches the end 20 used to create the reference signal image, within tolerances preset by the operator by means of keyboard 38, thumbwheel switches 39 or other input devices 40. If it does match, the wire end 20a is allowed to continue to move along the conveyor and be processed normally at station 22. If it does not match, however, an error signal indicating which wire segment 20a generated it is stored in an error signal memory area 44 by main processor 36. Then, when the wire end 20a arrives at station 22, the terminal attachment machine 23 is operated so as to prevent the machine from attaching a terminal to the defectively stripped wire end. Wire segment 13a is then conveyed beyond station 22 without having a terminal attached thereto. The terminal attachment machine 23 at station 22 is located a known number of conveyor steps or stations after inspection station 24. Thus by counting conveyor steps the terminal attachment machine 23 is prevented from operating on the defective wire end without affecting its operation on non-defective wire ends. This function could also be accomplished by any other suitable means such as time-delay calculations and so on.

In the embodiment shown in FIG. 2, error signal storage area 44 is connected only to main processor 36, while main processor 36 is connected to and controls the terminal attachment machine 23 at second station 22. Thus it is main processor 36 which keeps track of the location of defective wire end 20a. When end 20a reaches station 22, it is main processor 36 which tests error signal storage area 44 and, finding an error signal, prevents machine 23 from operating on the defective end 20a.

Figure 3:
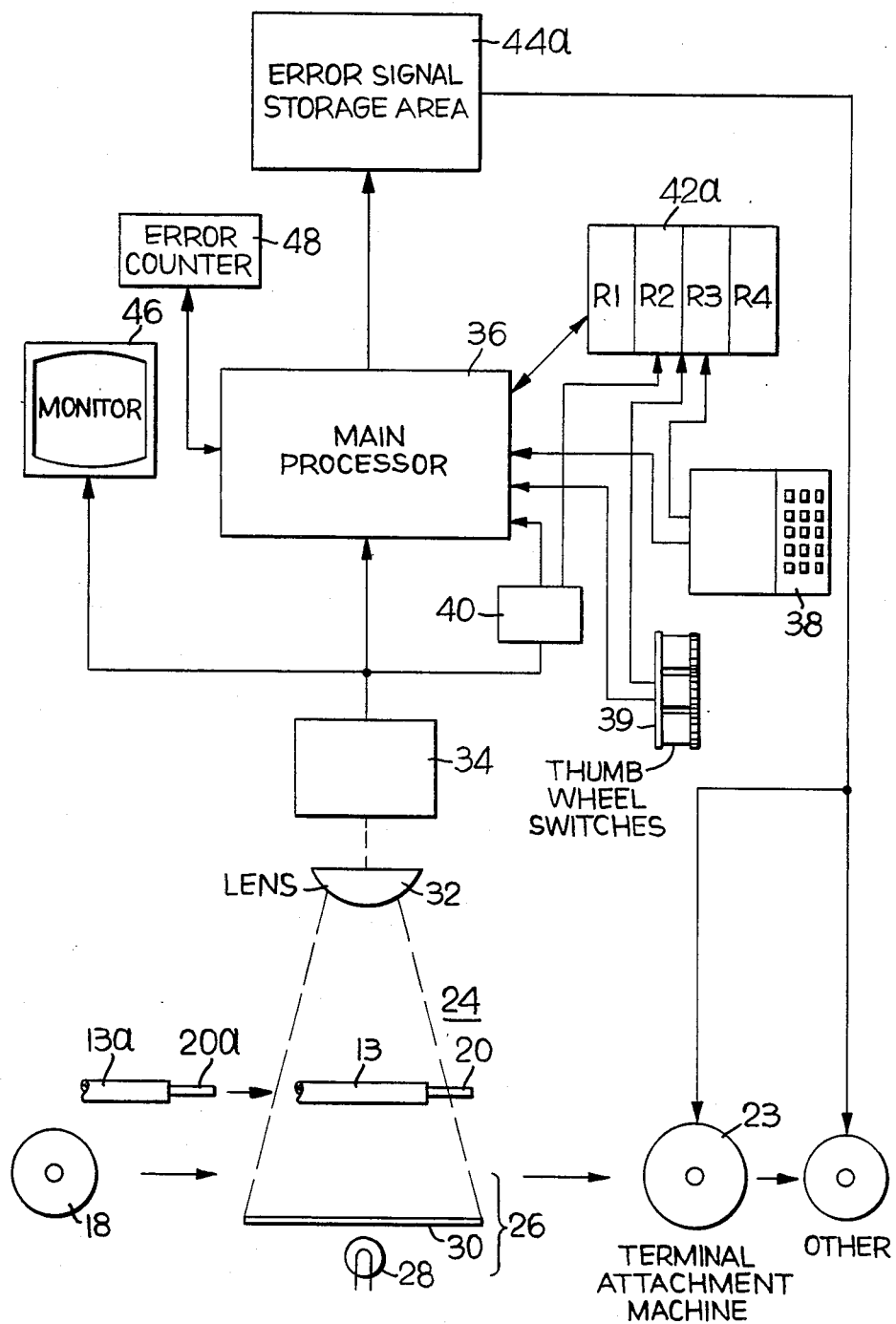
FIG. 3 is a schematic diagram of a control employing another embodiment of the present invention.

In the embodiment shown in FIG. 3, however, main processor 36 is not connected directly to the machine 23. Rather, on detection of a defectively stripped wire, main processor 36 merely sends an error signal to error signal storage area 44a. It is then error signal storage area 44a that keeps track of the location of the defectively stripped wire end 20a, and temporarily disables the terminal attachment machine 23 at the proper time so as to avoid operating on defective wire end 20a without affecting its operation on non-defective wire ends.

Also shown in FIG. 3 is a slightly different arrangement relating to reference signal storage area 42. In that figure, reference signal storage area 42a is capable of storing a plurality of different reference signals, in areas R1, R2, R3 and R4 thereof, for instance, all entered by the operator as described above with respect to FIG. 2. Then the reference signal which is the "current reference signal", that is, the reference signal against which the image signal is currently set to be compared, is determined by input from the operator via the various input devices. This is useful in situations where the apparatus 10 is used to process only a limited number of types of wires, and the different sets of parameters corresponding to the different reference signals need to be switched in and out easily and frequently. This arrangement would also be useful in an application where a plurality of types of wires were processed by the apparatus 10 in a regular, repetitive sequence. The different reference signals representing the different sets of parameters are then each accessed sequentially by main processor 36 to obtain reference signals, so as to properly process the various types of wires.

The arrangement of the reference signal storage area 42a shown in FIG. 3 could also be employed equally easily in the embodiment shown in FIG. 2.

Whether or not an error signal is generated, the image signal may be sent to a video monitor 46 for viewing by the human operator at his discretion. Thus the human operator has the opportunity to periodically monitor the performance of the inspection station 24.

In addition, the main processor 36 has an error counter 48 for counting the number of error signals sent to the error signal memory area 44. Using counter 48, the main processor 36 is programmed to stop the entire apparatus 10 upon the occurrence of a predetermined number of error signals. The main processor 36 will also stop the entire apparatus 10 if no wire ends at all are conveyed between the illuminated field 26 and the lens 32 for a predetermined number of conveyor steps.

While the apparatus hereinbefore described is effectively adapted to fulfill its intended objectives, it is to be understood that the invention is not intended to be limited to the particular preferred embodiments of wire processing apparatus herein set forth. Rather, it is to be taken as including all reasonable equivalents without departing from the scope of the appended claims.

I claim:

1. Wire processing apparatus for transporting wire segments along a path, for stripping insulation from the ends of said wire segments, and for attaching a wire terminal to the stripped ends of said wire segments, comprising:
   a conveyor for transporting wire segments in one direction in steps along said path;
   a wire stripping machine located at a first station along said conveyor for stripping insulation from at least one of the ends of said wire segments while said conveyor is stopped and said wire end is located at said first station to provide a stripped wire end having predetermined characteristics as to size and quality;
   a terminal attachment machine located at a second station along said conveyor which is downstream of said first station relative to said one direction, for attaching a wire terminal to said end of said wire segments after it has been stripped and while said conveyor is stopped and said wire end is located at said second station; and control means for controlling said apparatus by inspecting said wire end after it has been stripped but before a wire terminal is attached thereto and preventing attachment of a terminal if the inspection reveals that the stripped end of said wire does not meet said predetermined characteristics, said control means comprising:

means located at a third station between said first station and said second station for providing an optical image of the stripped end of said wire segment while said conveyor is stopped and said wire end is located at said third station;

means for converting said optical image into electrical image signals representing said optical image;

main processor means for receiving and processing signals representing said electrical image signals;

input means for providing reference signals representing said predetermined characteristics for a stripped wire end to said main processor means;

first memory means for receiving and storing said reference signals from said main processor means by means of a learn mode, wherein said main processor means, at a command of the operator, receives said image signals and converts them to said reference signals for storage in said first memory means;

said main processor means comparing said electrical image signals to said reference signals and providing error signals in the event of a discrepancy beyond preset tolerance limits indicating a defectively stripped wire end; and second memory means for receiving and storing said error signals;

said terminal attachment machine being prevented from attaching a terminal to the particular wire end located at its station in the event that said second memory means has received an error signal with respect to that particular wire end, indicating that the particular wire end is defective.

2. Wire processing apparatus according to claim 1 wherein said preset tolerance limits are entered by means of an operator-actuated keyboard.

3. Wire processing apparatus according to claim 1 wherein said preset tolerance limits are entered by means of a set of thumbwheel switches controlled by the operator.

4. Wire processing apparatus according to claim 2 or 3 further comprising video display means for displaying a video image representing said optical image.

5. Wire processing apparatus according to claim 4 further comprising counter means for counting the number of defective stripped ends and sending a signal to said main processor means to stop the entire apparatus upon the occurrence of a predetermined number of defective stripped ends.

6. Wire processing apparatus according to claim 5 wherein said means for providing an optical image comprises:

a light source; and an optical system positioned opposite said light source for receiving an optical image of each stripped wire end as said end is conveyed between said light source and said optical system, said optical system communicating with said means for converting said optical image into electrical image signals.

7. Wire processing apparatus according to claim 1 wherein said main processor means tests said second memory means when a wire end is at said terminal attachment machine and, in the event an error signal is stored there for said wire end, said main processor means disables said terminal atachment machine from attaching a terminal to said wire end.

8. Wire processing apparatus according to claim 1 wherein, when a wire end is at said terminal attachment machine, in the event an error signal is stored in said second memory means, said second memory means disables said terminal attachment machine from attaching a terminal to said wire end.

9. Wire processing apparatus according to claim 7 or 8 wherein said first memory means stores a plurality of reference signals corresponding to a plurality of respective sets of characteristics of wire ends and wherein the operator selects via said input means which set of characteristics to use as a reference signal for comparison to the image signal.

10. Wire processing apparatus according to claim 7 or 8 wherein said first memory means stores a plurality of reference signals corresponding to a plurality of respective sets of characteristics of wire ends, wherein said apparatus processes a plurality of types of wires in a regular repetitive sequence, and wherein said main processor means sequentially accesses said respective sets of characteristics to obtain reference signals for comparison against said sequence of types of wires.

11. Wire processing apparatus comprising:

a conveyor for transporting an insulated wire segment in steps along a path;

a wire stripping machine for stripping insulation from an end of said wire segment to provide a stripped wire segment end having predetermined characteristics;

a terminal attachment machine for attaching a wire terminal to said stripped wire segment end;

means located between said machines for providing an optical image of said stripped wire end when it moves therepast;

means for converting said optical image to image signals;

means for generating reference signals representing said predetermined characteristics;

main processor means for receiving, storing and recalling said reference signals, and for comparing said image signals to said reference signals and for providing error signals in the event of a discrepancy therebetween beyond preset tolerance limits, and for identifying that wire segment which caused said error signals;

said main processor means having a learn mode wherein, at a command of an operator, said main processor means receives said image signals and converts them to said reference signals for comparison to later image signals; and means for receiving said error signals and for preventing operation of said terminal attachment machine when said conveyor presents a stripped wire end which deviates from said predetermined characteristics to said terminal attachment machine.

12. Wire processing apparatus according to claim 11 wherein said preset tolerance limits are entered by means of an operator-actuated keyboard.

13. Wire processing apparatus according to claim 11 wherein said preset tolerance limits are entered by means of a set of thumbwheel switches controlled by the operator.

14. Wire processing apparatus according to claim 12 or 13 further comprising video display means for receiving said image signal and displaying a visual image of a stripped wire end based thereon.

15. Wire processing apparatus according to claim 14 further comprising counter means for counting the number of defective stripped ends and sending a signal to said main processor means to stop the entire apparatus upon the occurrence of a predetermined number of defective stripped ends.

16. Wire processing apparatus according to claim 15 wherein said means for providing an optical image comprises:
- a light source; and
- an optical system positioned opposite said light source for receiving an optical image of each stripped wire end as said end is conveyed between said light source and said optical system, said optical system communicating with said means for converting said optical image into electrical image signals.

* * * * *